United States Patent
Doucet et al.

(10) Patent No.: US 9,579,267 B2
(45) Date of Patent: Feb. 28, 2017

(54) COSMETIC WITH ENHANCED COLLAGEN I SYNTHESIS

(75) Inventors: Olivier Doucet, Roquebrune Cap Martin (FR); Dorothee Bernini, Monaco (MC); Cecile Robert, Nice (FR); Muriel Pujos, Nice (FR)

(73) Assignee: Coty Germany GmbH, Mainz (DE)

( * ) Notice: Subject to any disclaimer, the term of this patent is extended or adjusted under 35 U.S.C. 154(b) by 376 days.

(21) Appl. No.: 14/232,727

(22) PCT Filed: Jul. 13, 2012

(86) PCT No.: PCT/EP2012/063834
§ 371 (c)(1),
(2), (4) Date: Feb. 13, 2014

(87) PCT Pub. No.: WO2013/007827
PCT Pub. Date: Jan. 17, 2013

(65) Prior Publication Data
US 2014/0161855 A1    Jun. 12, 2014

(30) Foreign Application Priority Data
Jul. 14, 2011    (EP) .................... 11173985

(51) Int. Cl.
| | | |
|---|---|---|
| *A61K 8/14* | (2006.01) | |
| *A61K 8/41* | (2006.01) | |
| *A61K 8/67* | (2006.01) | |
| *A61K 8/73* | (2006.01) | |
| *A61Q 19/08* | (2006.01) | |
| *A61K 8/11* | (2006.01) | |
| *A61K 8/97* | (2006.01) | |
| *A61K 8/99* | (2006.01) | |
| *A61K 31/07* | (2006.01) | |

(52) U.S. Cl.
CPC .................. *A61K 8/14* (2013.01); *A61K 8/11* (2013.01); *A61K 8/416* (2013.01); *A61K 8/671* (2013.01); *A61K 8/731* (2013.01); *A61K 8/736* (2013.01); *A61K 8/97* (2013.01); *A61K 8/99* (2013.01); *A61K 31/07* (2013.01); *A61Q 19/08* (2013.01)

(58) Field of Classification Search
CPC .......... A61K 8/14; A61K 8/416; A61K 8/671; A61K 8/731; A61K 8/746; A61K 8/11; A61K 8/97; A61K 8/99
See application file for complete search history.

(56) References Cited

U.S. PATENT DOCUMENTS

| | | | |
|---|---|---|---|
| 6,183,774 B1 | 2/2001 | Aust et al. | |
| 2003/0206958 A1 | 11/2003 | Cattaneo et al. | |
| 2004/0096419 A1* | 5/2004 | Golz-Berner ............ | A61K 8/11 424/74 |
| 2008/0266065 A1* | 10/2008 | Kennedy ................ | G08B 7/062 340/332 |

FOREIGN PATENT DOCUMENTS

| | | |
|---|---|---|
| DE | 102010030001 | 12/2010 |
| EP | 2113241 | 11/2009 |
| WO | 2009053414 | 4/2009 |

OTHER PUBLICATIONS

International Search Report and Written Opinion of the ISA mailed on Jan. 7, 2013 in PCT Application No. PCT/EP2012/063834. (10 pages).

* cited by examiner

*Primary Examiner* — Ali Soroush
(74) *Attorney, Agent, or Firm* — Schwegman Lundberg & Woessner, P.A.

(57) ABSTRACT

A cosmetic including two different systems for procurement of actives in the human skin and enhancing the collagen I synthesis. The cosmetic with enhanced collagen I synthesis can include 0.001 to 2% by weight, related to the total weight of the cosmetic, of a first retinol-containing system including retinol encapsulated in a chitosan and carboxymethyl cellulose shell, 0.001 to 3.5% by weight, related to the total weight of the cosmetic, of a second retinol-containing system including cationic liposomes composed of phospholipids and with a quaternary fatty acid monoamine with $C_{21}$-$C_{23}$ alkyl residue and the difference to 100% by weight of cosmetic subsidiaries. Very small amounts of retinol in combination with both transport systems show a remarkable effect on the synthesis of collagen I in comparison with one or more other known combinations of retinol derivatives or encapsulated systems.

12 Claims, 1 Drawing Sheet

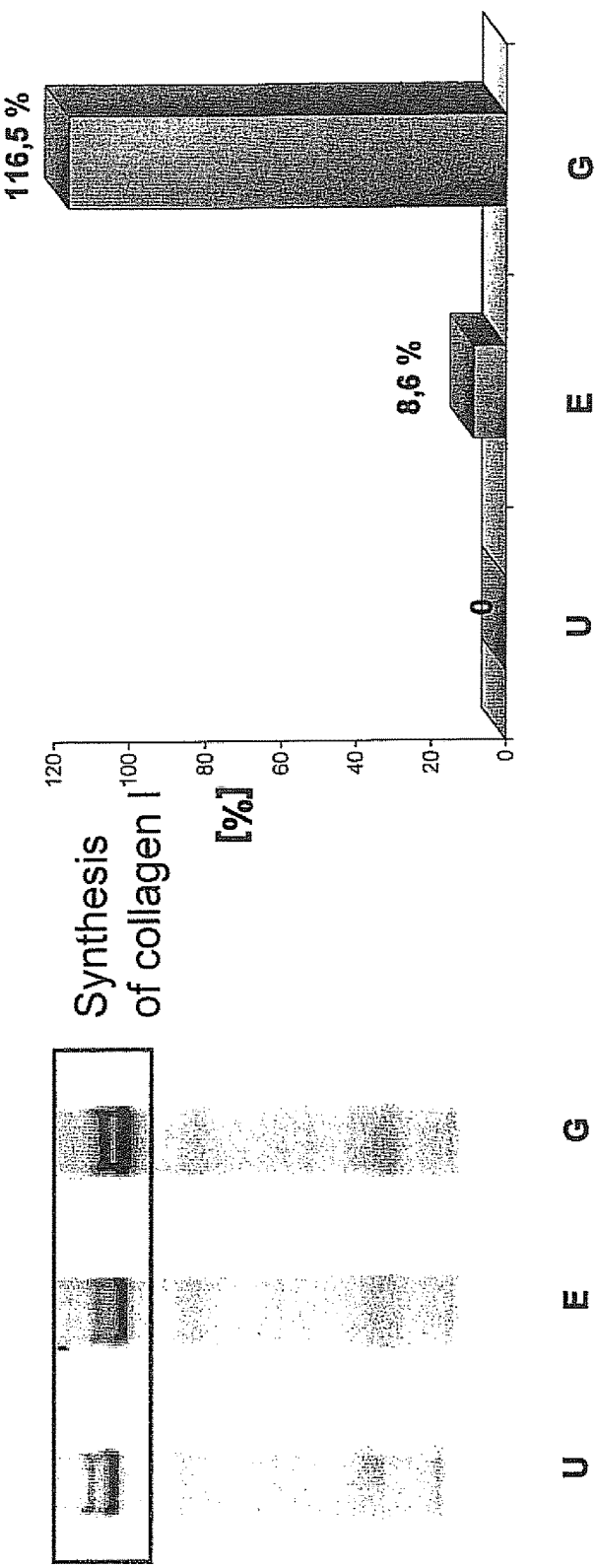

COSMETIC WITH ENHANCED COLLAGEN I SYNTHESIS

CROSS REFERENCE TO RELATED APPLICATIONS

This application is a §371 national stage entry of International Application No. PCT/EP2012/063834, filed on Jul. 13, 2012 and entitled "COSMETIC WITH ENHANCED COLLAGEN I SYNTHESIS", which claims priority to European Application No. 11173985.0, filed on Jul. 14, 2011, the entireties of which are incorporated herein by reference.

The invention relates to a cosmetic comprising two different systems for procurement of actives in the human skin and enhancing the collagen I synthesis.

EP 2113241 A2 describes a cosmetic product with some transport systems with actives comprising cyclodextrine, Chitosan/carboxymethyl cellulose microcapsules, lamellar systems and soy protein liposomes and showing a delayed release of retinol.

DE 10 2010 030 001 A1 refers to a cosmetic composition for dyeing hair and the use of a transport system of positively charged quaternary ammonium compounds of $C_{18}$-$C_{28}$ trimonium salts for direct dyes.

The object of the present invention is to improve the collagen I synthesis in the human skin. A further object is the improvement of the collagen I synthesis by small amounts of actives.

The invention is realised by a cosmetic with enhanced collagen I synthesis which comprises 0.001 to 2% by weight, preferably 0.01 to 1% by weight, more preferred 0.1 to 0.5% by weight, related to the total weight of the cosmetic, of a first retinol-containing system comprising retinol encapsulated in a chitosan and carboxymethyl cellulose (CMC) shell, 0.001 to 3.5% by weight, preferably 0.3 to 2.5% by weight, more preferred 1.5 to 2.5% by weight, related to the total weight of the cosmetic, of a second retinol-containing system comprising cationic liposomes composed of phospholipids and a quaternary fatty acid monoamine with a $C_{21}$-$C_{23}$ alkyl residue and the difference to 100% by weight of cosmetic subsidiaries.

It was found by the applicant that already very small amounts of retinol in combination with both transport systems show a remarkable effect on the synthesis of collagen I in comparison with one or more other known combinations of retinol derivatives or encapsulated systems. For instance, in a concentration of 0.5 to $15 \times 10^{-5}$% of pure retinol equivalent the collagen I synthesis was enhanced about 10-fold to about 15-fold. The reasons for this enhancement are not completely clear but it seems that a non-forseeable mutual influence of the two specially selected transport systems plays a leading part.

In the first retinol-containing system according to the invention the retinol is encapsulated in a chitosan/carboxymethyl cellulose shell and the retinol content is preferably in the range of 0.1 to 2.0% by weight, more preferred 0.1 to 1.5% by weight, related to the total weight of the first transport system. An advantageous product which can be used is Retinol-Primasphere® L2 of Cognis, Germany (INCI: Aqua (and) Glycine Soja (and) Retinol (and) Acrylates/C10-30 Alkyl Acrylate Crosspolymer (and) Chitosan (and) Cellulose Gum (and) Glycolic Acid (and) Polysorbate 20 (and) Sorbitan Oleate (and) Phenoxyethanol (and) Methylparaben (and) Ethylparaben (and) Butylparaben (and) Isobutylparaben (and) Propylparaben (and) BHT). The retinol content in Retinol-Primasphere® L2 is 1.1 to 1.3% by weight, related to the total weight of Retinol-Primasphere® L2.

In the second retinol-containing system of the invention the retinol is contained in liposomes which are formed by phospholipids, preferably by lecithin. The liposomes additionally possess positive charge carriers of the general formula R—N($R_1 R_2 R_3$)$^+$, wherein $R_1$, $R_2$ and $R_3$ are independently from each other methyl or ethyl, preferably methyl, and R represents $C_{21}$-$C_{23}$-alkyl, preferably $CH_3(CH_2)_{21}$-. The counter ions are preferably chloride ions. The retinol content of the second retinol containing system is preferably in the range of 0.1 to 3% by weight, more preferred 1.0 to 3.0% by weight.

In an especially preferred embodiment of the invention the cationic liposomes comprise Docosyltrimethylammonium chloride as charge carrier.

The cationic liposomes are prepared by solving the salt of the quarternary amine in an alcoholic solution of the phospholipide and adding the retinol to this solution. Then the resulting solution is added to a water phase and the pH value of the resulting emulsion is adjusted to 6 to 7 by adding a base. The INCI name of this product is Water (and) Alcohol (and) Lecithin (and) Retinol (and) Polysorbate 20 (and) Behentrimonium Chloride (and) Potassium Phosphate (and) Isopropyl Alcohol. These liposomes contain 1.5 to 2.2% by weight retinol and 1 to 5% by weight Docosyltrimethylammonium chloride, related to the total weight of the cationic liposomes.

It was found that preferred retinol contents in the range of 0.000114 to 0.0095% by weight, related to the total weight of the cosmetic and contained in the combined transport system of the invention already show remarkable effects on the collagen I synthesis.

Cosmetic subsidiaries which may be comprised by the cosmetic of the invention are e.g. radical scavengers, emulsifying agents, gelling agents, film-forming agents, sunscreens, stabilisers, boosters for the sun protection factor (SPF), moisturising substances, dyes, pigments, perfumes, conditioning agents, chelating agents, pH-value regulators, anti-inflammatory natural active agents, humectants, DNA repair agents etc.

In a preferred embodiment of the invention the cosmetic comprises radical scavengers, UV filters, emulsifying agents, moisturising substances, gel formers, SPF boosters, emollients, silicone oils, emulsion stabilisers, pH regulators, preservatives, DNA repair agents and/or pigments.

Additional cosmetic subsidiaries which can be used in the cosmetic of the invention include e.g. water, vitamins, enzymes, plant extracts, polymers, phospholipids, panthenol, allantoin, synthetic ethers and esters, fatty acids, monovalent and multivalent alcohols, silicones, minerals, oils especially plant oils, waxes, biotechnological extracts. Biotechnological extracts are e.g. PF CLR Repair Complex or Yeast Complex B (both of CLR, Chem. Lab. Dr. Kurt Richter GmbH, Berlin, Germany).

Especially preferred subsidiaries which may be comprised by the cosmetic of the invention are water, plant extracts and their mixtures, synthetic polymers, esters, ethers, fatty acids, monovalent and multivalent alcohols, silicones, silicates, pigments such as $TiO_2$, quartz and mica (trade name: Timiron splendid copper) and/or hyaluronic acid and salts thereof.

A cosmetic of the invention can advantageously contain radical scavengers such as folic acid and derivatives thereof, ubiquinone such as ubiquinone-10; flavones or flavonoids;

furthermore amino acids, such as histidine, tyrosine, tryptophan, and derivatives thereof; imidazole such as cis- or trans-urocaninic acid and their derivatives; peptides such as D,L-carnosine, D-carnosine, L-carnosine and their derivatives; hyaluronic acid; lycopene; uric acid and derivatives thereof; α-hydroxy acids such as citric acid, lactic acid, malic acid; α-hydroxy fatty acids such as palmitic acid, phytic acid, lactoferrin; mannose and their derivatives; liponic acid and their derivatives such as dihydro liponic acid; ferulic acid and their derivatives; thiols such as glutathione, cysteine and cystine.

The addition of the sodium salt of hyaluronic acid is especially preferred.

The term "radical scavengers" means for the present invention such substances which are able to scavenge free radicals such as superoxide anion radical ($O_2^-$), hydrogen peroxide ($H_2O_2$), hydroxyl radical (.OH), singulett oxygen ($^1O_2$), carbon centered (.CH—R) lipid radicals or L. radicals etc.

For the present invention the entirety of radical scavengers comprise a special plant extract mixture of liposomic encapsulated plant extracts of 1-4% Camellia Sinensis Leaf Extract, 1-4% Green Coffee Seed Extract, 1-4% Pongamia Pinnata Seed Extract, 1-4% Angelica Archangelica Root Extract, 1-4-% Citrus Aurantium Peel Extract, 2-10% phospholipids in an aqueous-alcoholic suspension wherein the alcohol content is in the range of 4-12%, wherein all concentrations are related to the weight of the radical scavenger mixture. The extracts are prepared by extraction with a monovalent or multivalent alcohol or a mixture of such alcohol(s) with water at room temperature (about 15 to 30° C.). This mixture may additionally comprise a mixture of vitamin E and C and derivatives thereof, An especially preferred vitamine mixture is PEG-8 & Tocopherol & Ascorbyl palmitate & Citric Acid & Ascorbic acid (trade name Oxynex K).

The share of such a radical scavenger mixture in the cosmetic of the invention is 0.05 to 2.0% by weight, related to the total weight of the composition, preferably 0.1 to 0.5% by weight.

Further preferred subsidiaries which may be comprised by the cosmetic of the invention are Hydrolyzed Soy Flour (trade name: Raffermine 2); a mixture of horse chestnut and caffeine; sodium hyaluronate; Euglena Gracilis Extract; and Bifida Ferment Lysate (trade name Repair Complex PF CLR).

The content of such subsidiaries is usually in the range of 0.009-0.2% by weight for each.

The cosmetic of the invention can be formulated as different cosmetic products by including the corresponding ingredients common for such products such as e.g. lotions, oils, creams, day creams, night creams, day care products with UV protection, gels, masks, balms, powders, eye-liftings, eye creams, tan glows, tinted creams, fillers, tissue masks, pre-sun products, sun products, after-sun products, self-tans, make-ups, compact powders, photoprotecting products, sprays, makeup-removers, cleansers, target products, primers, blush powders, bath products such as shower and bath gels or salts, lipsticks, deo sticks.

The especially preferred combination of Caffein and Horse Chestnut Extract (INCI: Glycerin & Water & Aesculus Hippocastanum Seed Extract; trade name: Phytami Marron D'Inde) is aimed for eye creams to stimulate the microcirculation in order to act on dark circles and puffiness.

The especially preferred ingredient Euglena Gracilis Extract of the algae Euglena gracilis is aimed for night creams of the invention to reinforce the ATP synthesis in cells at night and stimulate cell regeneration.

Emulsion products include multiple emulsions, micro emulsions and nano emulsions in the form of W/O, O/W, W/Si, Si/W, W/O/W, O/W/O, O/W/Si and W/Si/W emulsions (O=Oil, W=Water, Si=Silicone). Other products such as anhydrous systems like Si/O are also included.

Pre-sun products are e.g. pre-sun gels, pre-sun lotions, pre-sun creams or pre-sun oils. Sun products are gels, creams, lotions, oils, sprays or daily protective skin care products with different Sun Protection Factors (SPF) in the range from SPF 2 to SPF 50, e.g. SPF 6, SPF 10, SPF 15, SPF 20, SPF 25, SPF 30, SPF 50 and SPF 50+. The different SPFs are dependent on the kind and amount of UV filter substances.

Suitable cosmetic gel-forming agents for the preparation of a gel are e.g. carbomer, xanthan gum, carrageenan, acacia gum, guar gum, agar-agar, alginates and tyloses, magnesium aluminium silicates, carboxymethyl cellulose, hydroxyethyl cellulose, quaternized cellulose, quaternized guar, certain polyacrylates, such as acrylates/C10-30 alkyl acrylate cross polymer, polyvinyl alcohol, polyvinylpyrrolidone.

Especially preferred are according to the invention xanthan gum, Carbomer, Ammonium Acryloyldimethyltaurate/VP Copolymer Ammonium Acryloyldimethyltaurate/Beheneth-25 Methacrylate Crosspolymer Acrylates/C12-22 Alkyl Methacrylate Copolymer, Magnesium Aluminium Silicate, Sodium Acrylate/Sodium Acryloyldimethyl Taurate Copolymer, Hydroxyethyl Acrylate/Sodium Acryloyl Dimethyl Taurate Copolymer, Polyester-5 and Acrylates/Vinyl Neodeconoate Crosspolymer, Sodium Polyacrylate or Polyacrylamide/C13-14 Isoparaffin/Laureth 7/Styrene/Acrylate Copolymer Sodium Lauryl Sulfate or mixtures thereof.

For the preparation of sun products it is moreover advantageous to include into a cosmetic product of the invention together with the inventive transport systems corresponding water and/or oil soluble UVA or UVB filters or both. Advantageous oil-soluble UVB filters include 4-amino benzoic acid derivatives such as e.g. 4-(dimethylamino)-benzoic acid-(2-ethylhexyl)ester; esters of cinnamic acid such as e.g. 4-methoxy cinnamic acid (2-ethylhexyl)ester, benzophenone derivatives such as e.g. 2-hydroxy-4-methoxy benzophenone or mixtures thereof.

Preferred oil-soluble UV filters are Butyl-Methoxybenzoylmethane, Ethylhexyl Methoxycinnamate, Ethylhexyl Salicylate, and/or Bis-Ethyl Hexyl Phenol Methoxyphenyl Triazine.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters which may be used in the cosmetic of the present invention include dibenzoyl methane derivatives such as Butyl-Methoxybenzoylmethane.

Especially preferred are Butyl Methoxydibenzoylmethane, Ethylhexyl Methoxycinnamate, Ethylhexyl Salicylate, Octocrylene, Ethylhexyl Methoxycinnamate, Isoamyl-p-Methoxycinnamate, Ethylhexyltriazone, Diethylhexyl Butamido Triazone, Methylene Bis-Benzotriazolyl Tetramethylbutylphenol, Disodium Phenyl Dibenzimidazole Tetrasulfonate, Bis-Ethylhexyloxyphenol Methoxyphenyl Triazine and/or Benzophenone-3. Inorganic pigments as sunscreen filters are metal oxides such as $TiO_2$, $SiO_2$, $Fe_2O_3$, $ZrO_2$, $MnO$, $Al_2O_3$, which can also be used in mixtures thereof.

The cosmetic of the invention can also comprise tanning agents. Such tanning agents are e.g. isatin, glycerin aldehyde, meso-tartaric acid aldehyde, glutaraldehyde, erythrulose, pirazoline-4,5-dion derivatives, dihydroxyacetone (DHA) and/or 4,4-dihydroxy pirazoline-5-dion derivatives.

The cosmetic of the invention can also comprise humectants such as e.g. glycerin, butylene glycol, propylene glycol or mixtures thereof.

The cosmetic of the invention can also comprise moisturising, pores tightening or firming agents, mostly from plants and algae, e.g. hazel water, *Pisum Sativum* (Pea) Extract.

Further ingredients the cosmetic of the present invention can comprise are oils, emulsifiers, esters and pigments.

Oils used for the invention can be usual cosmetic oils such as e.g. mineral oil, hydrogenated polyisobutene, squalane from synthetic or natural sources, saturated or unsaturated vegetable oils, or mixtures of two or more thereof.

Especially suitable oils are, for example, silicone oils, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, castor oil, cocoa butter, Inca inchi oil, coconut oil, corn oil, cotton seed oil, olive oil, palm kernel oil, rapeseed oil, safflower seed oil, sesame seed oil, soybean oil, sunflower seed oil, wheat germ oil, grape kernel oil, kukui nut oil, Cameline oil, buriti oil, calendula oil, thistle oil or mixtures thereof.

Depending upon the oils selected, the cosmetic properties of a solid cosmetic of the invention such as softness, hardness or spreading effects can be affected.

Esters used in the cosmetic of the present invention can be esters of polyols. Suitable esters of polyols are esters of $C_{10}$-$C_{15}$ fatty acids and alcohols, esters of $C_{10}$-$C_{15}$ fatty acids and glycols, or esters of hydroxy fatty acids. Branched $C_{12}$-$C_{15}$ alkyl esters in conjunction with other esters such as di- or tri-esters of polyols are particularly advantageous in the oil phase, with esters of linear-chain alcohols and branched acids being particularly favourable. All these suitable esters are derived from primary alcohols. Preferred esters are Dicaprylyl Carbonate, Decyl Cocoate, Diisopropyl Sebacate, Dibutyl Adipate and Isopropyl Palmitate.

According to the invention suitable substances for the oil phase include Isohexadecane, PEG-40-Stearate, Sorbitan Tristearate, Behenyl Alcohol, Neopentyl Glycol Diheptanoate, Propylene Glycol Dicaprylate, Dioctyl Adipate, Cococaprylate/Caprate, Diethylhexyl Adipate, Diisopropyl Dimer Dilinoleate, Diisostearyl Dimer Dilinoleate, Isohexadecane, Butyrospermum Parkii (shea) Butter, $C_{12-13}$ Alkyl Lactate, Di-$C_{12-13}$ Alkyl Tartrate, Tri-$C_{12-13}$ Alkyl citrate, $C_{12-15}$ Alkyl Lactate, PPG Dioctanoate, Diethylene Glycol Dioctanoate, Meadowfoam Oil, Babassu Oil, Jojoba Oil, Rice Oil, $C_{12-15}$ Alkyl Oleate, Avocado Oil, Tridecyl Neopentanoate, Beeswax, Betearyl Alcohol and Polysorbate 60, $C_{18-26}$ Triglycerides, Cetearyl Alcohol & Cetearyl Glucoside, Acetylated Lanolin, VP/Eicosene Copolymer, Glyceryl Hydroxystearate, $C_{18-36}$ Acid Glycol Ester, with substances such as $C_{18-36}$ Triglycerides, Caprylic/Capric Triglyceride, Glyceryl Hydroxystearate and mixtures thereof. Also suitable and preferred are Cetyl Alcohol & Glyceryl Stearate & PEG 75 Stearate & Ceteth-20 & Steareth-20, Lauryl Glucoside & Polyglyceryl-2 Dipolyhydroxystearate, Beheneth-25, Polyamide-3 & Pentaerythrityl Tetra-Di-T-Butyl Hydroxycinnamate, Polyamide-4, PEG-100 Stearate, Potassium Cetylphosphate, Stearic Acid, Hectorites, Hydrogenated Polyisobutene, Behenyl Alcohol, Dicaprylyl Carbonate or mixtures of two or more thereof.

Especially preferred auxiliaries in the cosmetic of the present invention are oils and synthetic esters, ethers, waxes or alcohols such as e.g. vegetable oils, Dimethicone, Shea Butter, Polyglyceryl-3 Diisostearate, Dicaprylyl Carbonate, Beheneth-10, Hydrogenated Polyisobutene, Candelilla Wax, Mineral Oil, Petrolatum, Cetyl Alcohol, PEG-100 Stearate/Glycerylstearate, Stearyl Dimethicone, C12-15 Alkyl Benzoate, Caprylic/Capric Triglyceride and/or Hydrogenated Polydecene.

Preferred silicones of the cosmetic of the present invention are Cyclopentasiloxane/Dimethicone Crosspolymer, Dimethicone and Cyclopentasiloxane & Dimethiconol.

Preferred film-forming agents are e.g. Methyl Methacrylate Crosspolymer, Acrylates/Acrylamide Copolymer, Acrylates/VA Crosspolymer, PVP, Butylated PVP, Chitosan, Polyquaternium-13 to -42, etc.

The cosmetic according to the invention may preferably exist as O/W or W/O emulsion as well as emulsion from the above-mentioned type of multiple, micro or nano emulsions. Suitable emulsifiers for O/W emulsions are for instance addition products of 2-30 mol ethylene oxide to linear $C_8$-$C_{22}$ fatty alcohols, to $C_{12}$-$C_{22}$ fatty acids and to $C_8$-$C_{15}$ alkylphenols; $C_{12}$-$C_{22}$ fatty acid monoesters and diesters of addition products of 1-30 mol ethylene oxide to glycerin; glycerin monoesters and diesters as well as sorbitan monoester and diester of $C_6$-$C_{22}$ fatty acids, polyol- and polyglycerin ester; addition products of ethylene oxide to castor oil; as well as ampholytic tensides.

Suitable emulsifiers for W/O emulsions are for instance addition products of 2-15 mol ethylene oxide to castor oil, esters of $C_{12}$-$C_{22}$ fatty acids and glycerine, polyglycerine, glycols, pentaerythrite, sugar alcohols (e.g. sorbite), polyglucosides (e.g. cellulose), polyalkylene glycols, wool alcohols, copolymers of polysiloxan polyalkyl polyether.

Suitable emulsifiers for multiple emulsions and micro emulsions are for instance Tribehenin PEG-20 Esters, PEG-12 Dimethicone Crosspolymer, Lauryl PEG/PPG-18/18 Methicone, PEG-PPG-19/19 Dimethicone including Cyclopentasiloxane, Polyglyceryl-6 Dioleate and PEG-8 Caprylic/Capric Glycerides.

The cosmetic of the invention may also comprise pigments, pigment mixtures or powders with a pigment-like effect, also including those with a pearl-gloss effect. They may include, for example, iron oxides, aluminium silicates such as ochre, titanium dioxide, kaolin, manganese containing clays, silicium dioxide, quartz, zinc oxide, calcium carbonate, French chalk, nylon beads, ceramic beads, mica, expanded and non-expanded synthetic polymer powders, powdery natural organic compounds such as milled solid algae, milled plant parts, encapsulated and non-encapsulated cereal starches.

Further cosmetic subsidiaries which may be comprised by the cosmetic of the invention are waxes. The waxes may be selected among natural plant waxes, animal waxes, natural and synthetic mineral waxes and synthetic waxes. The cosmetic may include carnauba wax, candelilla wax, ozokerite, beeswax, montan wax, wool wax, ceresine, micro waxes, paraffin waxes, petrolatum, silicon wax, polyethylene glycol waxes or polyethylene glycolester waxes or mixtures thereof.

In an in use test with volunteers with sensitive skin and with particular sensitiveness to retinol products, a day cream formula was tested with very good results:

Texture: appreciated 91%, no sticky effect, fast penetration into the skin 91%.

The skin is comfortable: 91% of favourable appraisal; skin feels protected and nourished, immediate comfort.

Supple skin: 100% of favourable appraisal; very nice play time with soft finish

Softness the skin: 96% of favourable appraisal; velvety touch.

A further object of the invention is a method for enhancing the synthesis of collagen I in human skin, which comprises the application onto the human skin of a cosmetic with enhanced retinol potential which comprises 0.001 to 2% by weight, preferably 0.01 to 1% by weight, more preferred 0.1 to 0.5% by weight, related to the total weight of the cosmetic, of a first retinol-containing system comprising retinol encapsulated in a chitosan and carboxymethyl cellulose shell, 0.001 to 3.5% by weight, preferably 0.3 to 2.5% by weight, more preferred 1.5 to 2.5% by weight, related to the total weight of the cosmetic, of a second retinol-containing system comprising cationic liposomes composed of phospholipids and a quaternary fatty acid monoamine with a $C_{21}$-$C_{23}$ alkyl residue, and the difference to 100% by weight of cosmetic subsidiaries.

A further object of the present invention is the use of a composition for preparing a cosmetic which is improving the synthesis of collagen I in the human skin, which composition comprises 0.001 to 2% by weight, preferably 0.01 to 1% by weight, more preferred 0.1 to 0.5% by weight, related to the total weight of the cosmetic, of a first retinol-containing system comprising retinol encapsulated in a chitosan and carboxymethyl cellulose shell, 0.001 to 3.5% by weight, preferably 0.3 to 2.5% by weight, more preferred 1.5 to 2.5% by weight, related to the total weight of the cosmetic, of a second retinol-containing system comprising cationic liposomes composed of phospholipids and a quaternary fatty acid monoamine with a $C_{21}$-$C_{23}$ alkyl residue.

A further object of the present invention is a cosmetic for use in improving the synthesis of collagen I in the human skin, which cosmetic comprises 0.001 to 2% by weight, preferably 0.01 to 1% by weight, more preferred 0.1 to 0.5% by weight, related to the total weight of the cosmetic, of a first retinol-containing system comprising retinol encapsulated in a chitosan and carboxymethyl cellulose shell, 0.001 to 3.5% by weight, preferably 0.3 to 2.5% by weight, more preferred 1.5 to 2.5% by weight, related to the total weight of the cosmetic, of a second retinol-containing system comprising cationic liposomes composed of phospholipids and a quaternary fatty acid monoamine with a $C_{21}$-$C_{23}$ alkyl residue and the difference to 100% by weight of cosmetic subsidiaries.

The invention shall now be described in detail for the cosmetic composition of the invention by examples. All figures given as percentages are % by weight if not specified otherwise.

The enclosed drawings show in

FIG. 1 collagen I stimulation in percent according to Western Blot Test.

In the following examples basically INCI-names of the ingredients are used.

EXAMPLES 1-3

Anti Age Day Cream

| | Example 1 | Example 2 | Example 3 |
|---|---|---|---|
| Phase I | | | |
| Water | q.s. ad 100 | q.s. ad 100 | q.s. ad 100 |
| Mica, Silica, $TiO_2$ | 0.40 | 0.40 | 0.40 |
| Glycerin | 3.00 | 3.00 | 3.00 |
| Butylene Glycol | 3.00 | 3.00 | 3.00 |
| Xanthan Gum | 0.10 | 0.10 | 0.10 |
| Ammonium Acryloyldimetyltaurate/VP Copolymer | 0.30 | 0.30 | 0.30 |
| Methyl Methacrylate Crosspolymer | 2.00 | 2.00 | 2.00 |
| Preservative | 0.25 | 0.25 | 0.25 |
| Phase II | | | |
| Dicaprylyl Carbonate | 4.00 | 4.00 | 4.00 |
| Behenyl Alcohol | 1.00 | 1.00 | 1.00 |
| Beheneth-10 | 3.00 | 3.00 | 3.00 |
| Polyglyceryl-3 Diisostearate | 0.35 | 0.35 | 0.35 |
| Hydrogenated Polyisobutene | 3.50 | 3.50 | 3.50 |
| Shea Butter | 3.80 | 3.80 | 3.80 |
| Vegetable Oil & Hydrogenated Vegetable Oil & Candellila Wax | 0.80 | 0.80 | 0.80 |
| Phase III | | | |
| Dimethicone | 3.50 | 3.50 | 3.50 |
| Cyclopentasiloxane & Dimethicone Crosspolymer | 1.80 | 1.80 | 1.80 |
| Cyclopentasiloxane & Dimethiconol | 4.00 | 4.00 | 4.00 |
| Phase IV | | | |
| Microcapsules Retinol based on chitosan & CMC (Retinol-Primasphere L2) | 0.70 | 0.35 | 0.166 |
| Liposomes Retinol 2 based on quaternary ammonium compound | 2.12 | 2.33 | 0.375 |
| RPF complex* | 0.20 | 0.20 | 0.20 |
| Hydrolyzed Soy Flour Water & Quarz & Potassium Sorbate & Sorbic Acid & Phosphoric Acid | 0.10 | 0.10 | 0.10 |
| Preservatives | 0.10 | 0.10 | 0.10 |
| Preservatives | 1.10 | 1.10 | 1.10 |
| Fragrance | 0.30 | 0.30 | 0.30 |
| Polyacrylamide & Water & C13-14 Isoparaffin & Laureth 7 | 0.95 | 0.95 | 0.95 |

*RPF complex: Green Coffee Seed Extract (2%), *Camellia Sinensis* Leaf Extract (2%), *Pongamia Pinnata* Seed Extract (2%), *Angelica Archangelica* Root Extract (2%), *Citrus Aurantium* Peel Extract (1%), all in wt-% related to the weight of the RPF complex and encapsulated in lecithin liposomes and also comprising 5 to 10% by weight of an alcohol, and water and auxiliaries.

Process:

All ingredients of phase 1 and phase 2 were separately mixed and heated to about 70° C. Both phases were put together at 70° C. and stirred until homogeneity of the emulsion. Cool down to 50° C., adding all ingredients of phase 3 while stirring, then cool down to 30° C., adding all ingredients of phase 4 while stirring until homogeneity.

EXAMPLE 4

Comparative Test

Collagen-I by Western Blot

Normal fibroblasts were treated for 6 days with the ingredients E and G alone, diluted in a culture medium. Then collagen was extracted and collagen I was detected by using immunoblotting method with a chemiluminescence detection kit. The intensity of the bands of collagen I obtained on the treated cells was compared to the intensity of the bands of the non-treated cells. Moreover, the intensity of the bands was quantified by using an image analysis software.

The results are presented in FIG. 1.

The in vitro Western Blotting collagen-I synthesis shows the following results after an image analysis

| | | |
|---|---|---|
| (1) | Non-treated fibroblasts: | no activity |
| (2) | Ingredients E = Mixture of | |
| | Cyclodextrin with Retinol (Trade name: Cavamax ® W8) | |
| | lamellar stored retinol (Trade name: Probiol ®) | |
| | Chitosan/CMC encapsulated retinol (Trade name: Retinol-Primasphere ® L2) | |
| | Soy protein liposomes with retinol palmitate (Trade name: Cytovector ™) | |
| | (INCI: Laurdimonium Hydroxypropyl Hydrolyzed Soy Protein). | |
| | The total amount of pure retinol equivalent is $15.5 \times 10^{-5}\%$ | 8.6% |
| (3) | Ingredients G (according to the present invention) = Mixture of | |
| | Chitosan/CMC encapsulated retinol (Retinol-Primasphere ® L2) and Docosyltrimethylammonium Chloride/Lecithine encapsulated retinol (cationic liposomes) | |
| | The total amount of pure retinol is $11.4 \times 10^{-5}\%$ | 116.5% |

The results show a 13-fold enhancement from 8.6% to 116.5% when comparing results of mixture of ingredients E to mixture of ingredients G. The results are demonstrated in FIG. 1."U"=untreated (control), E and G are the ingredient mixtures.

In contrast to the used cationic liposome Docosyltrimethylammonium Chloride/Lecithin (4) of the invention, other cationic liposomes such as Lauryldimoniumhydroxylpropyl Hydrolyzed Soy Protein (5) (Cytovector™) show nearly no effect on the stimulation of the collagen I synthesis. (4) and (5) each loaded with $0.5 \times 10^{-5}\%$ retinol equivalent show a stimulation of (4)=30.6%
(5)=0.3% in comparison to untreated fibroblasts.

The invention claimed is:

1. Cosmetic with enhanced retinol potential which comprises
    0.001 to 2% by weight, related to the total weight of the cosmetic, of a first retinol-containing system comprising retinol encapsulated in a chitosan and carboxymethyl cellulose shell,
    0.001 to 3.5% by weight, related to the total weight of the cosmetic, of a second retinol-containing system comprising cationic liposomes composed of phospholipids and a quaternary fatty acid monoamine with a $C_{21}$-$C_{23}$ alkyl residue
    and the difference to 100% by weight of cosmetic subsidiaries.

2. Cosmetic according to claim 1, wherein the cosmetic comprises Hydrolyzed Soy Flour.

3. Cosmetic according to claim 1, wherein the cosmetic comprises Bifida Ferment Lysate.

4. Cosmetic according to claim 1, wherein the cosmetic comprises a mixture of the plant extracts Angelica Archangelica Root Extract, Camellia Sinensis Leaf Extract, Pongamia Pinnata Seed Extract, Coftea Arabica Seed Extract encapsulated in liposomes and together with 5-10% by weight of an alcohol, related to the weight of the mixture.

5. Cosmetic according to claim 1, wherein the subsidiaries are selected from antioxidants, radical scavengers, plant extracts, vitamins, UV filters, cosmetic oils, cosmetic esters, emulsifying agents, pigments, preservatives, water, gel formers, sodium hyaluronate, minerals and mixtures thereof.

6. Cosmetic according to claim 1, wherein the range of the first retinol-containing system in the cosmetic is 0.01 to 1.0% by weight.

7. Cosmetic according to claim 1, wherein the range of the second retinol-containing system in the cosmetic is 0.3 to 2.5% by weight.

8. Cosmetic according to claim 1, wherein the retinol content in the cosmetic is in the range of 0.000114 to 0.0095% by weight, related to the total weight of the cosmetic.

9. Cosmetic according to claim 1, wherein the cosmetic is a lotion, oil, cream, gel, mask, balm, powder, tan glow, pre-sun product, sun product, after-sun product, self-tan, make-up, compact powder, photo-protecting product or spray.

10. A method comprising using a composition for preparing a cosmetic with improved synthesis of collagen I in human skin, which composition comprises
    0.001 to 2% by weight, related to the total weight of the cosmetic, of a first retinol-containing system comprising retinol encapsulated in a chitosan and carboxymethyl cellulose shell,
    0.001 to 3.5% by weight, related to the total weight of the cosmetic, of a second retinol-containing system comprising cationic liposomes composed of a phospholipids and a quaternary fatty acid monoamine with a $C_{21}$-$C_{23}$ alkyl residue.

11. The method according to claim 10, wherein the composition is used for the preparation of a lotion, oil, cream, gel, mask, balm, powder, tan glow, pre-sun product, sun product, after-sun product, self-tan, make-up, compact powder, photo-protecting product or spray.

12. Method for enhancing the synthesis of collagen Tin the human skin, which comprises the application on the human skin of a cosmetic with enhanced retinol potential which comprises
    0.001 to 2% by weight, related to the total weight of the cosmetic, of a first retinol-containing system comprising retinol encapsulated in a chitosan and carboxymethyl cellulose shell,
    0.001 to 3.5% by weight, related to the total weight of the cosmetic, of a second retinol-containing system comprising cationic liposomes composed of phospholipide and a quaternary fatty acid monoamine with a $C_{21}$-$C_{23}$ alkyl residue
    and the difference to 100% by weight of cosmetic subsidiaries.

* * * * *